United States Patent [19]

Cantatore et al.

[11] Patent Number: 4,843,159
[45] Date of Patent: Jun. 27, 1989

[54] TRIAZINE DERIVATIVES OF PIPERIDINYLAMIDINES

[75] Inventors: Giuseppe Cantatore, Bitonto; Valerio Borzatta, Bologna, both of Italy

[73] Assignee: Ciba-Geigy Corporation, Ardsley, N.Y.

[21] Appl. No.: 59,650

[22] Filed: Jun. 8, 1987

[30] Foreign Application Priority Data

Jun. 16, 1986 [IT] Italy ................................ 20798 A/86

[51] Int. Cl.$^4$ ............................................. C07D 401/14
[52] U.S. Cl. ..................................... 544/198; 544/209; 544/113; 540/598; 540/575; 540/474
[58] Field of Search ...................... 544/198, 209, 113; 540/598, 575, 474

[56] References Cited

U.S. PATENT DOCUMENTS

| | | | |
|---|---|---|---|
| 4,086,204 | 4/1978 | Cassandrini et al. | 260/45.8 NT |
| 4,108,829 | 8/1978 | Cassandrini et al. | 260/45.8 NT |

FOREIGN PATENT DOCUMENTS

| | | |
|---|---|---|
| 2268011 | 11/1975 | France . |
| 60-84258 | 5/1985 | Japan . |
| 2176482 | 12/1986 | United Kingdom . |

*Primary Examiner*—John M. Ford
*Attorney, Agent, or Firm*—Harry Falber

[57] ABSTRACT

A compound of formula (I)

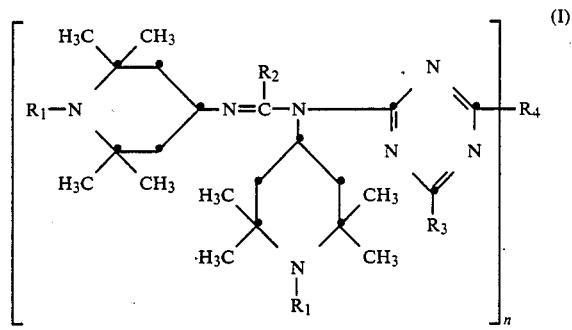

in which $R_1$ and $R_2$ are e.g. hydrogen or methyl, $R_3$ is e.g. a group

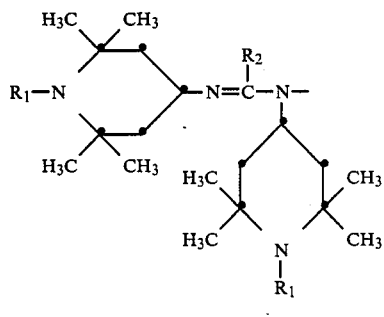

or a group $R_5X$— with $R_5$ being e.g. hydrogen, $C_1$–$C_{18}$-alkyl or $C_3$–$C_{18}$-alkenyl and X being e.g. —O—, —S— or

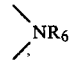

and $R_6$ is as defined for $R_5$, or $R_3$ represents a 5-membered to 7-membered nitrogen containing heterocyclic group with the free valency on the nitrogen, n is an integer from 2 to 6, and $R_4$ is a nitrogen containing organic radical of a valency equal to n.

The compounds of formula (I) are particularly effective in stabilizing organic material against oxidative, thermal and/or light induced degradation.

9 Claims, No Drawings

TRIAZINE DERIVATIVES OF PIPERIDINYLAMIDINES

The present invention relates to novel triazine derivatives of piperidinylamidines, the use thereof and to the organic material stabilized with the aid of said compounds against thermal, oxidative and/or light induced degradation.

It is known that synthetic polymers undergo progressive changes in their physical properties, such as loss of mechanical strength and colour changes, when they are exposed to sunlight or other sources of ultraviolet light. To retard the deleterious effect of ultraviolet radiation on synthetic polymers, it has been proposed to use various additives having light-stabilizing properties, such as certain benzophenone and benzotriazole derivatives, nickel complexes, alkylidenemalonates, cyanoacrylates and hindered amines. U.S. Pat. No. 4,086,204 and U.S. Pat. No. 4,108,829 describe piperidinyl-triazine compounds and the use thereof as light stabilizers.

GB Pat. No. 2,176,482 discloses formamidine derivatives containing piperidinyl groups and the use thereof as light stabilizers.

FR Pat. No. 2,268,011 describes substituted N,N'-diphenyl-formamidine compounds as light stabilizers and JP 85-84,258 discloses a process for the preparation of substituted N,N'-formamidine derivatives.

The present invention relates to compounds of formula (I)

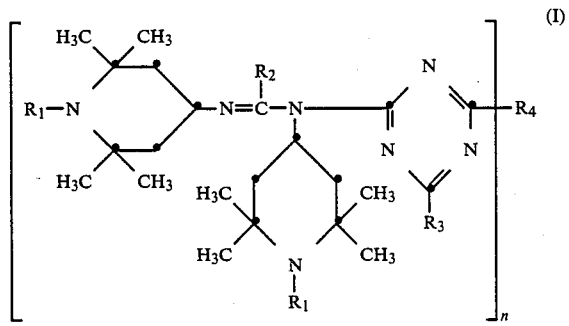

in which $R_1$ is hydrogen, O·, CN, NO, cyanomethyl, $C_1$–$C_{12}$-alkyl, $C_3$–$C_{12}$-alkenyl or $C_3$–$C_{12}$-alkynyl, with the proviso that the carbon atom attached to the nitrogen atom is a primary carbon atom, $C_7$–$C_{12}$aralkyl, $C_1$–$C_{12}$-acyl, 2,3-epoxypropyl, 2,3-dihydroxypropyl or OH-monosubstituted $C_2$–$C_6$-alkyl, $R_2$ is hydrogen, $C_1$–$C_{18}$-alkyl, $C_5$–$C_{18}$-cycloalkyl, $C_6$–$C_{18}$-aryl or $C_7$–$C_{18}$-aralkyl, $R_3$ is a group

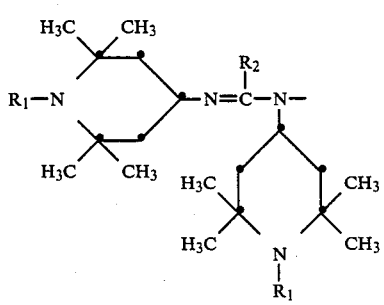

in which $R_1$ and $R_2$ are as defined above, or $R_3$ is a group $R_5X$— in which $R_5$ is hydrogen, $C_1$–$C_{18}$-alkyl, $C_2$–$C_6$-alkyl which is mono-substituted by OH, by $C_1$–$C_{18}$-alkoxy or by $C_2$–$C_{18}$-dialkylamino, $C_5$–$C_{18}$-cycloalkyl, $C_3$–$C_{18}$-alkenyl, $C_6$–$C_{18}$-aryl, $C_7$–$C_{18}$-aralkyl or a group of the formula (II)

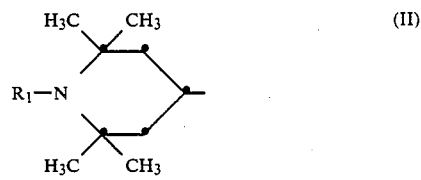

in which $R_1$ is as defined above, and X is —O—, —S— or

$R_6$ being as defined for $R_5$, or $R_3$ represents a 5-membered to 7-membered nitrogen containing heterocyclic group with the free valency on the nitrogen, and n is an integer from 2 to 6, if n is 2, $R_4$ is a group

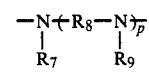

in which p is zero or 1, $R_7$ and $R_9$, which are identical or different, are as defined for $R_5$, and $R_8$ is a direct bond, $C_2$–$C_{18}$-alkylene, $C_5$–$C_{18}$-cycloalkylene, $C_6$–$C_{18}$-arylene, $C_7$–$C_{18}$-aralkylene or $C_4$–$C_{14}$-alkylene which is interrupted in the chain by one or two oxygen atoms or by one or two

groups, in which $R_{10}$ is hydrogen, $C_1$–$C_{12}$-alkyl, $C_6$–$C_{12}$-cycloalkyl or a group of the formula (II), or $R_4$ is the divalent radical of a 5-membered to 7-membered heterocyclic compound with two nitrogen atoms and the free valencies on the nitrogen atoms, or $R_4$ is

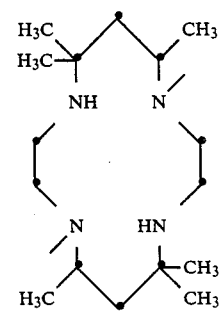

or

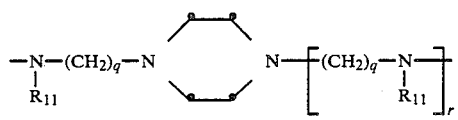

in which $R_{11}$ is as defined for $R_{10}$, q is an integer from 2 to 6 and r is zero or 1, if n is 3, $R_4$ is

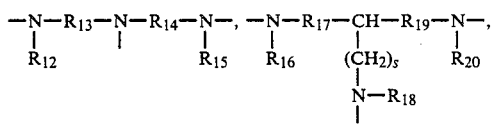

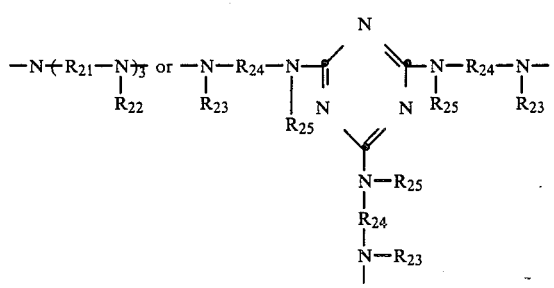

in which $R_{12}$, $R_{15}$, $R_{16}$, $R_{18}$, $R_{20}$, $R_{22}$, $R_{23}$ and $R_{25}$, which are identical or different, are as defined for $R_{10}$, and $R_{13}$ and $R_{14}$, which are identical or different, are $C_2$–$C_{12}$-alkylene or $C_4$–$C_{14}$-alkylene which is interrupted in the chain by an

group, $R_{17}$, $R_{19}$, $R_{21}$ and $R_{24}$, which are identical or different, are $C_2$–$C_{12}$-alkylene and s is zero or 1, if n is 4, 5 or 6, $R_4$ is a group

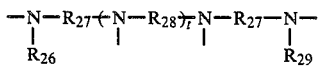

in which $R_{26}$ and $R_{29}$, which are identical or different, are as defined for $R_{10}$, and $R_{27}$ and $R_{28}$, which are identical or different, are $C_2$–$C_{12}$-alkylene and t is 1, 2 or 3, or, if n is 4, $R_4$ is additionally a group

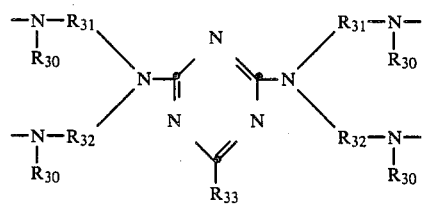

in which $R_{30}$ is as defined for $R_{10}$, $R_{31}$ and $R_{32}$, which are identical or different, are $C_2$–$C_{12}$-alkylene and $R_{33}$ is as defined for $R_3$, or, if n is 6, $R_4$ is additionally a group

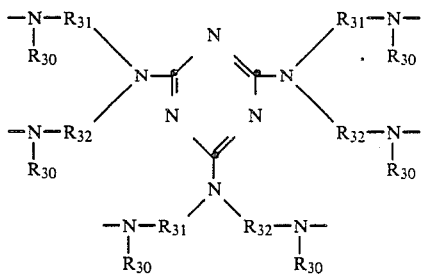

in which $R_{30}$, $R_{31}$ and $R_{32}$ are as defined above.

$R_1$, $R_{10}$, $R_{11}$, $R_{12}$, $R_{15}$, $R_{16}$, $R_{18}$, $R_{20}$, $R_{22}$, $R_{23}$, $R_{25}$, $R_{26}$, $R_{29}$ and $R_{30}$ as $C_1$–$C_{12}$-alkyl are for example methyl, ethyl, propyl, isopropyl, butyl, isobutyl, t-butyl, pentyl, hexyl, heptyl, octyl, 2-ethylhexyl, decyl or dodecyl. $C_1$–$C_4$-alkyl which may be straight chain or branched is preferred. $R_1$ as methyl is especially preferred.

$R_1$ as $C_3$–$C_{12}$-alkenyl is for example allyl, 2-methally, 2-butenyl, 2-hexenyl or 10-undecenyl. Allyl is especially preferred.

$R_1$ as $C_3$–$C_{12}$-alkynyl may be preferably propargyl.

$R_1$ as $C_7$–$C_{12}$-aralkyl is for example benzyl, methylbenzyl, t-butyl-benzyl or hydroxybenzyl. $C_7$–$C_{10}$-phenylalkyl unsubstituted or substituted at the phenyl ring by alkyl and/or by OH is preferred. Benzyl and benzyl substituted by $C_1$–$C_4$-alkyl and/or by OH are especially preferred.

$R_1$ as $C_1$–$C_{12}$-acyl may be an aliphatic or aromatic $C_1$–$C_{12}$-acyl group. $C_1$–$C_{12}$-alkanoyl, $C_3$–$C_{12}$-alkenoyl, $C_3$–$C_{12}$-alkynoyl, benzoyl and benzoyl substituted by $C_1$–$C_4$-alkyl and/or by OH are preferred. Examples are formyl, acetyl, propionyl, butyryl, caproyl, capryloyl, caprinoyl, lauroyl, benzoyl, acryloyl, methacryloyl and crotonyl.

$R_1$ as OH- monosubstituted $C_2$–$C_6$-alkyl is for example 2-hydroxyethyl, 2-hydroxypropyl or 3-hydroxypropyl.

$R_2$, $R_5$, $R_6$, $R_7$ and $R_9$ as $C_1$–$C_{18}$-alkyl are for example methyl, ethyl, propyl, isopropyl, butyl, isobutyl, 2-butyl, t-butyl, pentyl, isopentyl, hexyl, heptyl, 2-heptyl, octyl, 2-ethylhexyl, nonyl, decyl, undecyl, dodecyl, tridecyl, tetradecyl, pentadecyl, hexadecyl, heptadecyl or octadecyl. $R_2$ is preferably $C_1$–$C_4$-alkyl, in particular methyl.

$R_2$, $R_5$, $R_6$, $R_7$ and $R_9$ as $C_5$–$C_{18}$-cycloalkyl are preferably a cycloalkyl group of the formula

with a being an integer from 4 to 11. Said cycloalkyl group may optionally be substituted by $C_1$–$C_4$-alkyl. Examples are cyclopentyl, cyclohexyl, methylcyclohexyl, dimethyl-cyclohexyl, trimethylcyclohexyl, t-butylcyclohexyl, cyclooctyl and cyclododecyl. Cyclohexyl unsubstituted or substituted by $C_1$–$C_4$-alkyl is especially preferred.

$R_{10}$, $R_{11}$, $R_{12}$, $R_{15}$, $R_{16}$, $R_{18}$, $R_{20}$, $R_{22}$, $R_{23}$, $R_{25}$, $R_{26}$, $R_{29}$ and $R_{30}$ as $C_6$–$C_{12}$-cycloalkyl are preferably a cycloalkyl group of the formula

with a being an integer from 5 to 6. Said cycloalkyl group may optionally be substituted by $C_1$–$C_4$-alkyl. Examples are cyclohexyl, methylcyclohexyl, dimethylcyclohexyl, trimethylcyclohexyl, t-butylcyclohexyl cyclooctyl and cyclododecyl. Cyclohexyl unsubstituted or substituted by $C_1$–$C_4$-alkyl is especially preferred.

$R_2$, $R_5$, $R_6$, $R_7$ and $R_9$ as $C_6$–$C_{18}$-aryl may be preferably phenyl unsubstituted or substituted by $C_1$–$C_4$-alkyl, $C_1$–$C_4$-alkoxy and/or OH, or may be naphthyl unsubstituted or substituted by $C_1$–$C_4$-alkoxy. Preferred examples are phenyl, methylphenyl, dimethylphenyl, trimethylphenyl, ethylphenyl, t-butylphenyl, methoxyphenyl, ethoxyphenyl, hydroxyphenyl and 3,5-di-t-butyl-4-hydroxyphenyl with phenyl being especially preferred.

$R_2$, $R_5$, $R_6$, $R_7$ and $R_9$ as $C_7$–$C_{18}$-aralkyl may be 7–$C_{10}$-phenylalkyl unsubstituted or substituted at the phenyl ring by $C_1$–$C_4$-alkyl and/or OH. Examples are benzyl, methylbenzyl, t-butylbenzyl, hydroxybenzyl, 3,5-di-t-butyl-4-hydroxybenzyl and 2-(3,5-di-t-butyl-4-hydroxyphenyl)ethyl. Benzyl unsubstituted or substituted is preferred.

$R_5$, $R_6$, $R_7$ and $R_9$ as $C_3$–$C_{18}$-alkenyl are for example allyl, butenyl, 2-methallyl, hexenyl, undecenyl, or oleyl.

$R_5$, $R_6$, $R_7$ and $R_9$ as $C_2$–$C_6$-alkyl which is monosubstituted by OH, by $C_1$–$C_{18}$-alkoxy or by $C_2$–$C_{18}$-dialkylamino are for example 2-hydroxy-ethyl, 2-hydroxypropyl, 3-hydroxypropyl, 2-ethoxyethyl, 2-butoxyethyl, 2-octyloxyethyl, 2-dodecyloxyethyl, 3-methoxypropyl, 3-ethoxypropyl, 3-butoxypropyl, 3-octyloxypropyl, 3-dodecyloxypropyl, 4-butoxybutyl, 2-diethylaminoethyl, 2-dibutylaminoethyl, 3-diethylaminopropyl and 3-dibutylaminopropyl.

$R_8$ as $C_2$–$C_{18}$-alkylene is for example ethylene, propylene, trimethylene, tetramethylene, pentamethylene, 2,2-dimethyltrimethylene, hexamethylene, trimethylhexamethylene, octamethylene, decamethylene or dodecamethylene. $C_2$–$C_6$-alkylene is preferred.

$R_8$ as $C_5$–$C_{18}$-cycloalkylene may be a saturated hydrocarbon group with two free valencies and at least one cyclic unit.

$R_8$ as $C_5$–$C_{18}$-cycloalkylene is for example cyclohexylene or cyclo-hexylene substituted by $C_1$–$C_4$-alkyl or may be alkylene-cyclo-hexylene-alkylene with 8 to 18 carbon atoms, cyclohexylene-alkylene-cyclohexylene with 13 to 18 carbon atoms or alkylidenedicyclo-hexylene with 14 to 18 carbon atoms. Preferred examples are cyclo-hexylene, cyclohexylenedimethylene, methylenedicyclohexylene and isopropylidenedicyclohexylene.

$R_8$ as $C_6$–$C_{18}$-arylene is preferably 1,2-phenylene, 1,3-phenylene or 1,4-phenylene.

$R_8$ as $C_7$–$C_{18}$-aralkylene is preferably xylylene.

$R_8$ as $C_4$–$C_{14}$-alkylene which is interrupted in the chain by one or two oxygen is for example 4-oxaheptane-1,7-diyl, 4,7-dioxadecane-1,10-diyl, 4,9-dioxadodecane-1,12-diyl.

$R_{13}$, $R_{14}$, $R_{17}$, $R_{19}$, $R_{21}$, $R_{24}$, $R_{27}$, $R_{28}$, $R_{31}$ and $R_{32}$ as $C_2$–$C_{12}$-alkylene are for example ethylene, propylene, trimethylene, tetramethylene, hexamethylene, octamethylene, decamethylene or dodecamethylene. $C_2$–$C_6$-alkylene is preferred.

$R_{13}$ and $R_{14}$ as $C_4$–$C_{14}$-alkylene which is interrupted in the chain by an

group are for example 3-azapentane-1,5-diyl, 3-azahexane-1,6-diyl or 4-azaheptane-1,7-diyl.

If $R_3$ and $R_{33}$ are a 5-membered to 7-membered nitrogen containing heterocyclic group with the free valency on the nitrogen, this group is preferably a saturated heterocyclic group with N and/or O as hetero atoms. Illustrative examples are 1-pyrrolidinyl, piperidino, morpholino, 1-hexahydroazepinyl and 4-methyl-1-piperazinyl.

If $R_4$, when n is 2, is a 5-membered to 7-membered heterocyclic group with two nitrogen atoms and the free valencies on the nitrogen atoms, this group is preferably a saturated heterocyclic group. Illustrative examples are

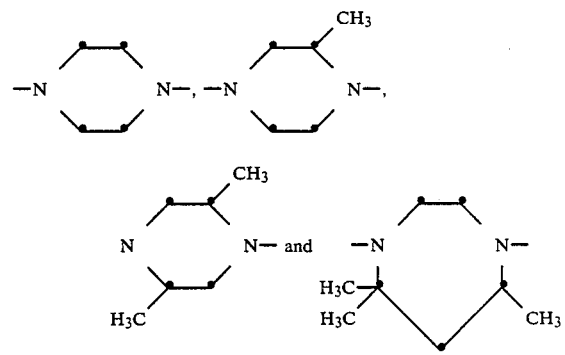

If $R_4$, when n is 2, is a group of the formula

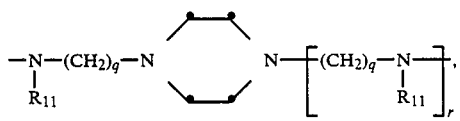

preferred examples are:

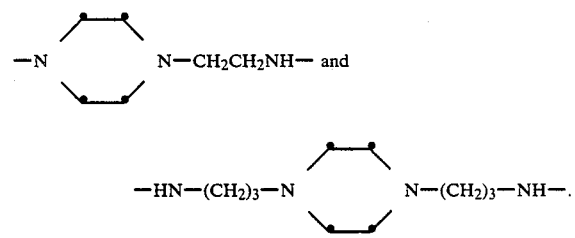

The group of the formula (II) is preferably 2,2,6,6-tetramethyl-4-piperidinyl or 1,2,2,6,6-pentamethyl-4-piperidinyl.

n is 2, 3, 4, 5 or 6, in particular 2, 3 or 4.

p is 0 or 1, preferably 1.

q is 2, 3, 4, 5 or 6, in particular 2.

r is 0 or 1, preferably 0.

$R_1$ is preferably hydrogen, $C_1$–$C_4$-alkyl, allyl, benzyl or acetyl, in particular hydrogen or methyl.

$R_2$ is preferably hydrogen, $C_1-C_{12}$-alkyl, cyclohexyl or phenyl, in particular hydrogen or methyl.

$R_3$ is preferably a group

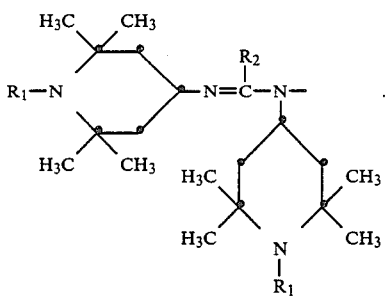

Those compounds of the formula (I) are preferred, wherein $R_1$ is hydrogen, methyl, allyl, benzyl or acetyl, $R_2$ is hydrogen, $C_1-C_{12}$-alkyl, $C_6-C_9$-cycloalkyl or $C_6-C_9$-aryl, $R_3$ is a group

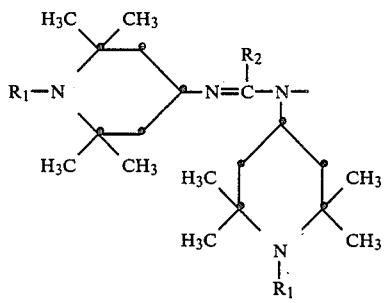

in which $R_1$ and $R_2$ are as defined above, a group $R_5X-$ with $R_5$ being hydrogen, $C_1-C_8$-alkyl, $C_6-C_9$-cycloalkyl, allyl or a group of the formula (II) and X being —O— or

where $R_6$ is hydrogen, $C_1-C_8$-alkyl, $C_6-C_9$-cycloalkyl, allyl or a group of the formula (II), or $R_3$ is 1-pyrrolidinyl, piperidino, morpholino or 1-hexahydroazepinyl and n is an integer from 2 to 6, and, if n is 2, $R_4$ is a group

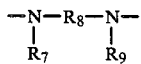

in which $R_7$ and $R_9$, which are identical or different, are hydrogen, $C_1-C_{12}$-alkyl, $C_6-C_9$-cycloalkyl, allyl or a group of the formula (II) and $R_8$ is $C_2-C_6$-alkylene, $C_6-C_{15}$-cycloalkylene, phenylene, xylylene or $C_4-C_{12}$-alkylene which is interrupted in the chain by one or two oxygen atoms or by one or two

groups, or $R_4$ is

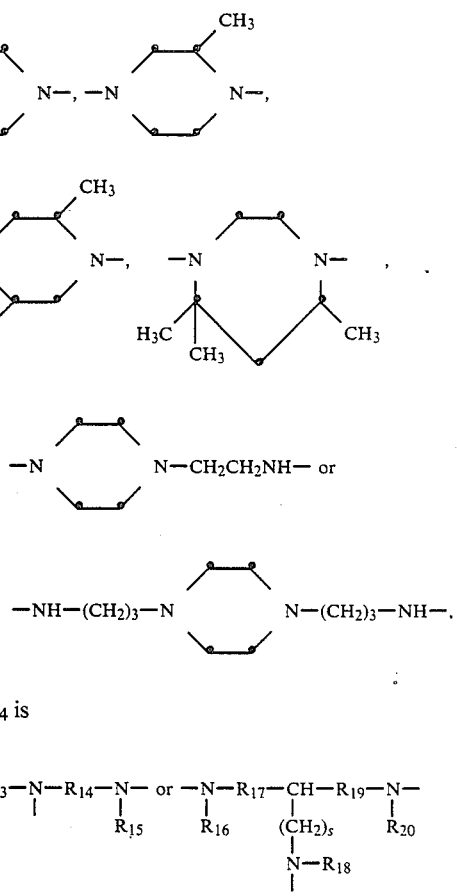

if n is 3, $R_4$ is

in which $R_{12}$, $R_{15}$, $R_{16}$, $R_{18}$ and $R_{20}$, which are identical or different, are hydrogen, $C_1-C_{12}$-alkyl, $C_6-C_9$-cycloalkyl or a group of the formula (II), $R_{13}$ and $R_{14}$, which are identical or different, are $C_2-C_6$-alkylene or $C_4-C_6$-alkylene which is interrupted in the chain by an $$\diagdown_{NH}\diagup$$

group, $R_{17}$ and $R_{19}$, which are identical or different, are $C_2-C_6$-alkylene and s is zero or 1, if n is 4, 5 or 6, $R_4$ is a group

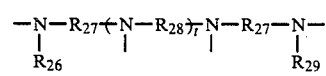

in which $R_{26}$ and $R_{29}$, which are identical or different, are hydrogen, $C_1-C_{12}$-alkyl, $C_6-C_9$-cycloalkyl or a group of the formula (II), $R_{27}$ and $R_{28}$, which are identical or different, are $C_2-C_6$-alkylene and t is 1, 2 or 3.

Those compounds of formula (I) are of interest, wherein $R_3$ is a group

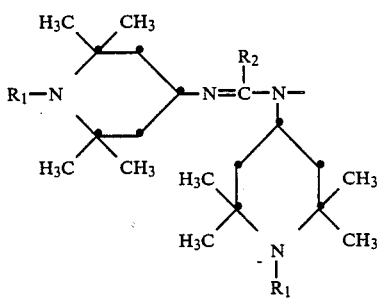

with $R_1$ being hydrogen, methyl, allyl, benzyl or acetyl and $R_2$ being hydrogen, $C_1-C_{12}$-alkyl, cyclohexyl or phenyl, or $R_3$ is a group $R_5X$— with $R_5$ being hydrogen, $C_1-C_8$-alkyl, cyclohexyl, allyl or a group of the formula (II) and X being —O— or $$\diagdown_{\diagup} NR_6,$$

where $R_6$ is hydrogen, $C_1-C_8$-alkyl, cyclohexyl, allyl or a group of the formula (II), or $R_3$ is 1-pyrrolidinyl, piperidino, morpholino or 1-hexahydroazepinyl and n is an integer from 2 to 6, and, if n is 2, $R_4$ is a group $$-\underset{R_7}{\overset{}{N}}-R_8-\underset{R_9}{\overset{}{N}}-$$

in which $R_7$ and $R_9$, which are identical or different, are hydrogen, $C_1-C_{12}$-alkyl, cyclohexyl, allyl or a group of the formula (II) and $R_8$ is $C_2-C_6$-alkylene, cyclohexylene, methylenedicyclohexylene, phenylene, xylylene or $C_4-C_{12}$-alkylene which is interrupted in the chain by one or two oxygen atoms or by one or two $$\diagdown_{\diagup} NH$$

groups, or $R_4$ is

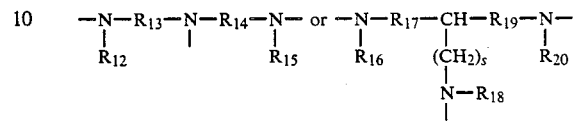

if n is 3, $R_4$ is one of the groups $$-\underset{R_{12}}{\overset{}{N}}-R_{13}-\underset{R_{15}}{\overset{}{N}}-R_{14}-\underset{R_{16}}{\overset{}{N}}- \text{ or } -\underset{R_{16}}{\overset{}{N}}-R_{17}-\underset{\underset{\underset{R_{18}}{\overset{}{N}}}{(CH_2)_s}}{\overset{}{CH}}-R_{19}-\underset{R_{20}}{\overset{}{N}}-$$

in which $R_{12}$, $R_{15}$, $R_{16}$, $R_{18}$ and $R_{20}$, which are identical or different, are hydrogen, $C_1-C_{12}$-alkyl, cyclohexyl or a group of the formula (II), $R_{13}$ and $R_{14}$, which are identical or different, are $C_2-C_6$-alkylene or $C_4-C_6$-alkylene which is interrupted in the chain by an $$\diagdown_{\diagup} NH$$

group, $R_{17}$ and $R_{19}$, which are identical or different, are $C_2-C_6$-alkylene and s is zero or 1, if n is 4, 5 or 6, $R_4$ is a group $$-\underset{R_{26}}{\overset{}{N}}-R_{27}\!\!\left(\!\!-\underset{}{\overset{}{N}}-R_{28}\!\!\right)_{\!\!t}\!\!\underset{}{\overset{}{N}}-R_{27}-\underset{R_{29}}{\overset{}{N}}-$$

in which $R_{26}$ and $R_{29}$, which are identical or different, are hydrogen, $C_1-C_{12}$-alkyl, cyclohexyl or a group of the formula (II), $R_{27}$ and $R_{28}$, which are identical or different, are $C_2-C_6$-alkylene and t is 1, 2 or 3.

Those compounds of formula (I) are particularly preferred, wherein $R_1$ is hydrogen or methyl, $R_2$ is hydrogen or methyl, $R_3$ is a group

[structure similar to formula above with $R_1$, $R_2$ substituents on piperidinyl rings]

in which $R_1$ and $R_2$ are hydrogen or methyl and n is an integer from 2 to 4, and,
if n is 2, $R_4$ is a group $$-\underset{R_7}{\overset{}{N}}-R_8-\underset{R_9}{\overset{}{N}}-$$

in which $R_7$ and $R_9$, which are identical or different, are hydrogen, $C_1-C_4$-alkyl, cyclohexyl, 2,2,6,6-tetramethyl-4-piperidinyl or 1,2,2,6,6-pentamethyl-4-piperidinyl and $R_8$ is $C_2-C_6$-alkylene, $C_6-C_{13}$-cycloalkylene or $C_4-C_{12}$-alkylene which is interrupted in the chain by one or two oxygen atoms or by one or two

groups, or $R_4$ is

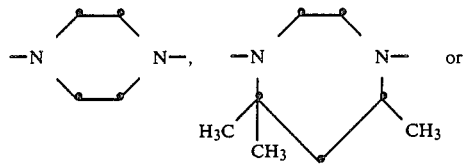

if n is 3, $R_4$ is a group

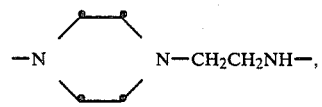

in which $R_{12}$ and $R_{15}$, which are identical or different, are hydrogen, $C_1$–$C_4$-alkyl, cyclohexyl, 2,2,6,6-tetramethyl-4-piperidinyl or 1,2,2,6,6-pentamethyl-4-piperidinyl, and $R_{13}$ and $R_{14}$, which are identical or different, are $C_2$–$C_6$-alkylene or $C_4$–$C_6$-alkylene which is interrupted in the chain by an

group, if n is 4, $R_4$ is a group

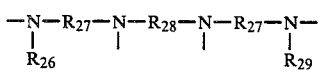

in which $R_{26}$ and $R_{29}$, which are identical or different, are hydrogen, $C_1$–$C_4$-alkyl, cyclohexyl, 2,2,6,6-tetramethyl-4-piperidinyl or 1,2,2,6,6-pentamethyl-4-piperidinyl, and $R_{27}$ and $R_{28}$, which are identical or different, are $C_2$–$C_6$-alkylene.

Also preferred are those compounds of formula (I), wherein $R_1$ and $R_2$ are hydrogen, $R_3$ is a group

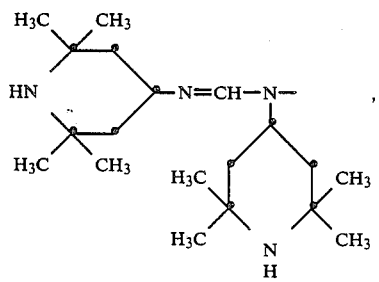

n is 2, 3 or 4, and, if n is 2, $R_4$ is a group

in which $R_7$ and $R_9$, which are identical or different, are hydrogen, methyl or 2,2,6,6-tetramethyl-4-piperidinyl and $R_8$ is —$(CH_2)_{2-6}$—, methylenedicyclohexylene, 4,7-dioxadecane-1,10-diyl or 4,7-diazadecane-1,10-diyl, or $R_4$ is a group

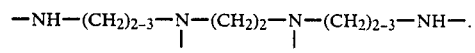

if n is 3, $R_4$ is a group

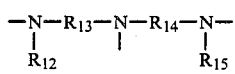

in which $R_{13}$ is a group —$(CH_2)_{2-3}$— and $R_{14}$ is a group —$(CH_2)_{2-3}$— or 3-aza-hexane-1,6-diyl, and, if n is 4, $R_4$ is a group

—NH—$(CH_2)_{2-3}$—N—$(CH_2)_2$—N—$(CH_2)_{2-3}$—NH—.

According to a further preferred embodiment $R_1$ and $R_2$, which are identical or different, are hydrogen or methyl, $R_3$ is a group

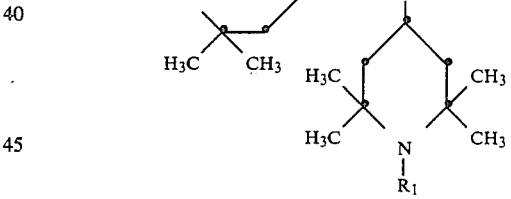

in which $R_1$ and $R_2$ are as defined above or $R_3$ is a group $R_5X$— in which $R_5$ is $C_1$–$C_8$-alkyl, $C_2$–$C_6$-alkyl which is monosubstituted by $C_1$–$C_6$-alkoxy or is allyl and X is $>NR_6$ with $R_6$ being hydrogen or $C_1$–$C_8$-alkyl or $R_3$ is morpholine, and n is an integer from 2 to 4, and, if n is 2, $R_4$ is a group

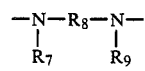

in which $R_7$ and $R_9$, which are identical or different, are hydrogen, $C_1$–$C_4$-alkyl or 2,2,6,6-tetramethyl-4-piperidinyl, $R_8$ is methylenedicyclohexylene, $C_2$–$C_6$- alkylene or $C_4$-$C_{12}$-alkylene which is interrupted in the chain by one or two oxygen atoms or by one or two

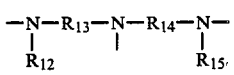

or $R_4$ is a group

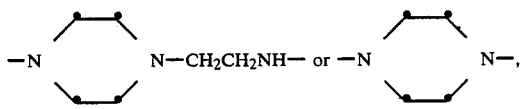

if n is 3, $R_4$ is

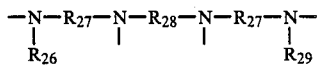

in which $R_{12}$ and $R_{15}$ are hydrogen and $R_{13}$ and $R_{14}$, which are identical or different, are $C_2$-$C_6$-alkylene or $C_4$-$C_6$-alkylene which is interrupted in the chain by one

group, and, if n is 4, $R_4$ is

—N—R$_{27}$—N—R$_{28}$—N—R$_{27}$—N—
 |                  |
 R$_{26}$              R$_{29}$ in which $R_{26}$ and $R_{29}$ are hydrogen and $R_{27}$ and $R_{28}$, which are identical or different, are $C_2$-$C_6$-alkylene.

Preferred examples of compounds of formula (I) are: N,N'-bis-[2,4-bis-[N'',N'''-bis-(2,2,6,6-tetramethyl-4-piperidinyl)-formamidino]-1,3,5-triazin-6-yl]-1,6-hexanediamine, N,N'-bis-[2,4-bis-[N'',N'''-bis-(2,2,6,6-tetramethyl-4-piperidinyl)-formamidino]-1,3,5-triazin-6-yl]-4,4'-methylene-bis-(cyclohexylamine), N,N'-bis-[2,4-bis-[N'',N'''-bis-(2,2,6,6-tetramethyl-4-piperidinyl)-formamidino]-1,3,5-triazin-6-yl]-N-methyl-1,3-propanediamine, N,N'-bis-[2,4-bis-[N'',N'''-bis-(2,2,6,6-tetramethyl-4-piperidinyl)-formamido]-1,3,5-triazin-6-yl]-4,7-dioxadecane-1,10-diamine, N,N',N''-tris-[2,4-bis-[N''',N$^{IV}$-bis-(2,2,6,6-tetramethyl-4-piperidinyl)-formamidino]-1,3,5-triazin-6-yl]-3-azapentane-1,5-diamine or N,N',N'',N'''-tetrakis-[2,4-bis-[N$^{IV}$,N$^V$-bis-(2,2,6,6-tetramethyl-4-piperidinyl)-formamidino]-1,3,5-triazin-6-yl]-4,7-diazadecane-1,10-diamine.

The compounds of formula (I) can be prepared by analogy to processes known per se, for example, by reacting cyanuric chloride in any order with the compounds of the formulae (III), (IV) and (V)

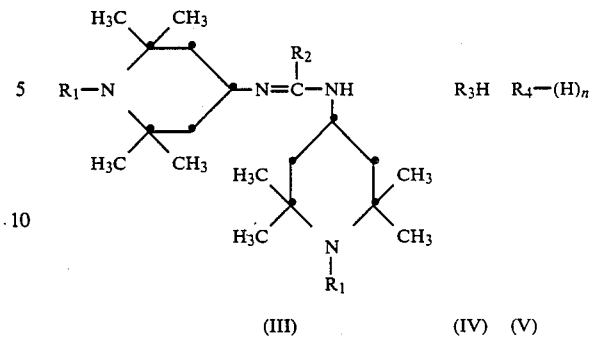

(III)  (IV)  (V)

in which $R_1$, $R_2$, $R_3$, $R_4$ and n are as defined above.

In detail, according to procedure A (scheme 1), cyanuric chloride can be reacted, for example, with equivalent quantities of compound (III) and compound (IV), the chlorotriazine of formula (VI) being formed, which is conveniently reacted with compound (V) in a molar ratio of (VI):(V)=n:1, the compounds of the formula (I) being obtained.

Scheme 1

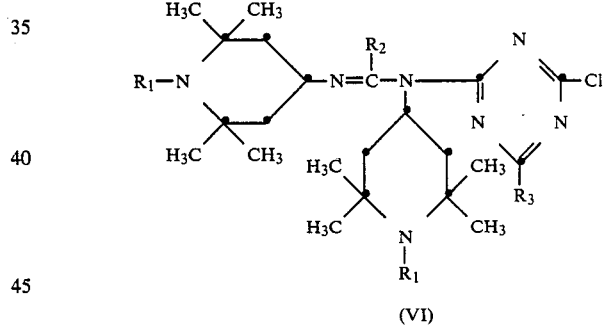

(VI)

n(VI) + (V) ⟶ compounds of the formula (I).  (b)

According to procedure B (scheme 2), cyanuric chloride can be reacted, for example, with the reagent of formula (V) in a molar ratio of cyanuric chloride:(V)=n:1, the compound of the formula (VII) being formed which is conveniently reacted with n moles of compound (III) and n moles of compound (IV), compounds of the formula (I) being obtained.

Scheme 2

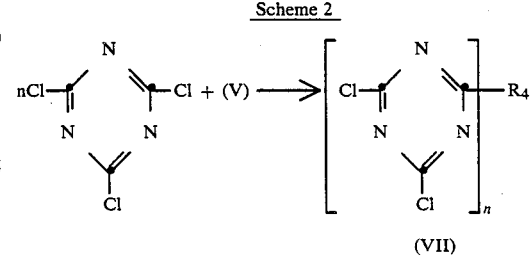

(VII)

-continued
Scheme 2

(VII) $\xrightarrow{n(III),n(IV)}$ compounds of the formula (I).  (b)

The reactions according to both procedures are preferably carried out in inert solvents, for example acetone, methyl ethyl ketone, methyl isobutyl ketone, dioxane, tetrahydrofuran, dibutyl ether, benzene, toluene, xylene, trimethylbenzene, ethylbenzene, decalin, octane, decane, chlorobenzene or N-methylpyrrolidone, in the presence of an organic or inorganic base, preferably sodium or potassium hydroxide or carbonate, in a quantity at least equivalent to the hydrochloric acid liberated in the reaction.

The substitution of the first chlorine in the cyanuric chloride conveniently takes place at a temperature between −30° and 40° C., preferably between −10° and 20° C., the substitution of the second chlorine preferably takes place between 40° and 100° C., in particular between 50° and 90° C., and the substitution of the third chlorine preferably takes place between 100° and 200° C., in particular between 120° and 180° C.

The ratio of the reagents is preferably theoretical, particularly in the substitution of the first and second chlorine of the cyanuric chloride, but an excess of up to 20% of reagent is also possible in the substitution of the third chlorine.

The various stages of the reactions can be carried out in one and the same reactor and in the same reaction medium, without isolation of the intermediates; nevertheless, it is also possible to separate the intermediates out and to use them after isolation in the following reactions.

The amidines of the formula (III), which are the starting materials for obtaining the compounds of the formula (I), can also be prepared by analogy to known processes, for example, by reacting 2 moles of a piperidinylamine (VIII) with 1 mole of the ortho-ester (IX), in which R' is preferably $C_1$–$C_4$-alkyl, the alcohol R'OH being separated off:

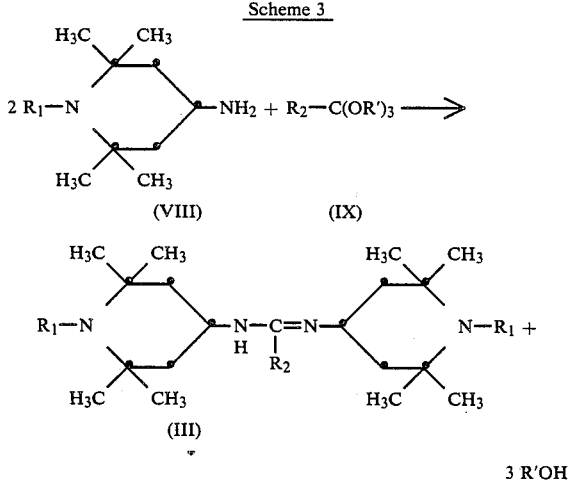

Scheme 3

This reaction can be carried out with or without an inert solvent at a temperature of between 80° and 250° C.

The compounds of formula (I) are effective in stabilizing organic materials, in particular synthetic polymers and copolymers, against thermal, oxidative and/or light induced degradation.

Substrates in which the compounds of formula (I) are particularly useful are polyethylene and polypropylene.

In general, polymers which can be stabilized include:

1. Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE and linear low density polyethylene (LLDPE).

2. Mixtures of the polymers mentioned under (1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefine and diolefines with each other or with other vinyl monomers, such as, for example, ethylene/propylene, linear low density polyethylene (LLDPE) and its mixtures with low density polyethylene (LDPE), propylene/butene-1, ethylene/hexene, ethylene/ethylpentene, ethylene/heptene, ethylene/octene, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylne with propylene and a diene, such as hexadiene, dicyclopentadiene or ethylidenenorbornene; as well as mixtures of such copolymers and their mixtures with polymers mentioned in (1) above, for example polypropylene/ethylene-propylene-copolymers, LDPE/EVA, LDPE/EAA, LLDPE/EVA and LLDPE/EAA.

3a. Hydrocarbon resins (for example $C_5$–$C_9$) and hydrogenated modifications thereof (for example tackyfiers).

4. Polystyrene, poly-(p-methylstyrene), poly-(α-methylstyrene).

5. Copolymers of styrene or α-methylstyrene with dienes or acrylic derivatives, such as, for example, styrene/butadiene, styrene/acrylonitrile, styrene/alkyl methacrylate, styrene/maleic anhydride, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under (8) with each other or with other unsaturated monomers, such as, for instance, acrylonitrile/butadien, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine; as well as their copolymers with olefins mentioned in (1) above.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer; polyacetals modified with thermoplastic polyurethanes, acrylates or MBS.

13. Polyphenylene oxides and sulfides, and mixtures of polyphenylene oxides with polystyrene or polyamides.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylene diamine and isophthalic or/and terephthalic acid and optionally an elastomer as modifier, for example poly-2,4,4,-trimethylhexamethylene terephthalamide or poly-m-phenylene isophthalamide. Further copolymers of the aforementioned polyamide with polyolefins, olefin copolymers, ionomers or chemically bonded or grafted elastomers; or with polyethers, such as for instance, with polyethylenee glycol, polypropylene glycol or polytetramethylene glycols. Polyamides or copolyamides modified with EPDM or ABS. Polyamides condensed during processing (RIM-polyamide systems).

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2,-(4-hydroxyphenyl)-propane] terephthalate and polyhydroxybenzoates as well as block-copolyether-esters derived from polyethers having hydroxyl end groups.

18. Polycarbonates and polyester-carbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyesteracrylates.

24. Alkyd resins, polyester resins or acrylate resins in admixture with melamine resins, urea resins, polyisocyanates or epoxide resins as crosslinking agents.

25 Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or the cellulose ethers, such as methylcellulose; rosins and their derivatives.

27. Mixtures of polymers as mentioned above, for example PP/EPDM, Polyamide 6/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/-butadiene copolymers.

The compounds of formula (I) are particularly effective as light stabilizers for polypropylene fibres and tapes and for low-density polyethylene films. The compounds of the formula (I) can be mixed with the organic material to be stabilised in various proportions depending on the nature of the polymer, on the end use and on the presence of other additives.

In general, it is advantageous to employ from 0.01 to 5% by weight of the compounds of the formula (I), relative to the weight of the polymers, preferably from 0.05 to 1%. The compounds of formula (I) can be incorporated into the polymeric materials via various processes, such as dry blending in the form of powders, or wet mixing in the form of solutions or suspensions, or mixing in the form of a master-batch; in these operations, the polymer can be employed in the form of powder, granules, a solution, a suspension or in the form of a latex.

The polymers stabilized with the products of the formula (I) can be used for the preparation of moulded articles, films, tapes, fibres, monofilaments, surface-coatings and the like.

The stabilized polymer compositions of the invention may optionally also contain various conventional additives, such as antioxidants, UV absorbers, nickel stabilizers, pigments, fillers, plasticizers, antistatic agents, flameproofing agents, lubricants, corrosion inhibitor and metal deactivators.

Preferred conventional additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4methylphenyl]terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl)sulfide, isooctyl 3,5-di-tert-butyl-4-hydroxybenzylmercaptoacetate, bis(4-tert-butyl-3-hydroxy-2,6-dimethylbenzyl)dithiolterephthalate, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl)isocyanurate.

1.6. Acylaminophenols, for example anilide of 4-hydroxylauric acid, anilide of 4-hydroxystearic acid, 2,4-bis(octylmercapto)-6-(3,5-di-tert-butyl-4-hydroxyanilino)-s-triazine, octyl N-(3,5-di-tert-butyl-4-hydroxyphenyl)carbamate.

1.7. Esters of β-(3,5-di-tert-butyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl)isocyanurate, thiodiethylene glycol, N,N'-bis(hydroxyethyl)oxalic acid diamide.

1.8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl)isocyanurate, thiodiethylene glycol, N,N'-bis(hydroxyethyl)oxalic acid diamide.

1.9. Esters of β-(3,5-dicyclohexyl-4-hydroxyphenyl)-propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl)isocyanurate, thiodiethylene glycol, N,N'-bis(hydroxyethyl)oxalic acid diamide.

1.10. Amides of β-(3,5-di-tert-butyl-4-hydroxyphenyl)propionic acid e.g. N,N'-bis(3,5-di-tert-butyl-4-hydroxyphenylpropionyl)hexamethylene-diamine, N,N'-bis(3,5-di-tert-butyl-4-hydroxyphenylpropionyl)-trimethylene-diamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis(α,α-dimethylbenzyl) derivatives.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example, 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, e.g. of the methyl or ethyl ester, nickel complexes of ketoximes, e.g. of 2-hydroxy-4-methylphenyl undecyl ketoneoxime, nickel complexes of 1-phenyl-4-lauroyl-5-hydroxypyrazole, with or without additional ligands.

2.6. Sterically hindered amines, for example bis(2,2,6,6-tetramethylpiperidyl)sebacate, bis(1,2,2,6,6- pentamethylpiperidyl)sebacate, bis(1,2,2,6,6-pentamethylpiperidyl)n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butane tetracarboxylate, 1,1'-(1,2-ethanediyl)bis(3,3,5,5-tetramethylpiperazinone).

2.7. Oxalic acid diamides, for example 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-disubstituted oxanilides and mixtures of o- and p-ethoxy-disubstituted oxanilides.

3. Metal deactivators, for example N,N'-diphenyloxalic acid diamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic acid dihydrazide.

4. Phosphites and phosphonites, for example triphenyl phosphite, diphenylalkyl phosphites, phenyldialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, tristearyl sorbitol triphosphite, tetrakis(2,4-di-tert-butylphenyl) 4,4'-biphenylene diphosphonite, 3,9-bis(2,4-di-tert-butylphenoxy)-2,4,8,10-tetraoxa-3,9-diphosphaspiro[5.5]undecane.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctyadecyl disulfide, pentaerythritol tetrakis(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

8. Nucleating agents, for example, 4-tert.butyl-benzoic acid, adipic acid, diphenylacetic acid.

9. Fillers and reinforcing agents, for example, calcium carbonate, silicates, glass fibres, asbestos, talc, kaolin, mica, barium sulfate, metal oxides and hydroxydes, carbon black, graphite.

10. Other additives, for example, plasticisers, lubricants, emulsifiers, pigments, optical brighteners, flameproofing agents, antistatic agents and blowing agents.

The following examples illustrate the embodiments of this invention.

EXAMPLE 1

(A) The preparation of 2-chloro-4,6-bis-[N,N'-bis-(2,2,6,6-tetramethyl-4-piperidinyl)-formamidino]-1,3,5-triazine 64.5 g (0.2 mol) of N,N'-bis-(2,2,6,6-tetramethyl-4-piperidinyl)-formamidine are added slowly to a solution of 18.44 g (0.1 mol) of cyanuric chloride in 500 ml of xylene cooled to 10° C., maintaining the temperature between 10° and 15° C.

After the end of the addition, the mixture is heated for 2 hours at 50°–55° C., 53 g (0.5 mol) of anhydrous ground $Na_2CO_3$ are added, and the mixture is heated for 3 hours at 70° C. and then filtered hot.

A white solid precipitates from the filtered solution, and this is separated off by filtration and dried.

The product thus obtained has a melting point of 206°–207° C.

Analysis for $C_{41}H_{74}ClN_{11}$. Calculated: Cl 4.69%. Found: Cl 4.71%.

(B) Preparation of N,N'-bis[2,4-bis-[N'',N'''-bis-(2,2,6,6-tetramethyl-4-piperidinyl)-formamidino]-1,3,5-triazin-6-yl]-1,6-hexanediamine 45.4 g (0.06 mol) of 2-chloro-4,6-bis-[N,N'-bis-(2,2,6,6-tetramethyl-4-piperidinyl)-formamidino]-1,3,5-triazine, 3.5 g (0.03 mol) of 1,6-hexanediamine, 3.2 g (0.08 mol) of ground NaOH and 300 ml of xylene are heated for 3 hours under reflux and then for further 16 hours while separating off the water of reaction.

The mixture thus obtained is evaporated in vacuo (26.7 mbar) and the white mass is washed with plenty of water and finally treated with warm acetone.

After drying, the product has a melting point of 299°–300° C.

Analysis for $C_{88}H_{162}N_{24}$. Calculated: C 67.91%; H 10.49%; N 21.60%. Found: C 67.51%; H 10.38%; N 21.12%.

EXAMPLE 2

Preparation of N,N'-bis-[2,4-bis-[N'',N'''-bis-(2,2,6,6-tetramethyl-4-piperidinyl)-formamidino]-1,3,5-triazin-6-yl]-4,4'-methylene-bis-(cyclohexylamine)

64.5 g (0.2 mol) of N,N'-bis (2,2,6,6-tetramethyl-4-piperidinyl)-formamidine are added slowly to a solution of 18.44 g (0.1 mol) of cyanuric chloride in 500 ml of xylene cooled to 10° C., the temperature being maintained between 10° and 15° C.

Afer the end of the addition, the mixture is heated at 50°–55° C. for 2 hours, 84.8 g (0.8 mol) of anhydrous ground $Na_2CO_3$ are added, and heating is continued for 3 hours at 70° C.

A solution of 10.52 g (0.05 mol) of 4,4'-methylene-bis-(cyclohexylamine) in 40 ml of xylene is then added and the mixture is heated under reflux for 3 hours and then for further 16 hours while separating off the water of reaction.

The mixture is then filtered hot, and the organic solution is evaporated in vacuo (26.7 mbar).

The solid obtained is washed with warm acetone and dried.

The product obtained has a melting point of 224°–228° C.

Analysis for $C_{95}H_{172}N_{24}$. Calculated: C 69.13%; H 10.50%; N 20.37%. Found: C 68.52%; H 10.46%; N 20.22%.

EXAMPLES 3-14

Following the procedure described in Example 2, the following compounds of the formula

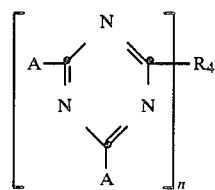

are prepared

| Example No. | n | A | R₄ | Melting point (°C.) |
|---|---|---|---|---|
| 3 | 2 | (tetramethylpiperidinyl-N=CH-N- with HN-tetramethylpiperidine group) | $-N(CH_3)-(CH_2)_3-NH-$ | 195-196 (crystallized from acetone) |
| 4 | 2 | (same as Ex. 3) | $-NH-(CH_2)_3-O-(CH_2)_2-O-(CH_2)_3-NH-$ | 259-264 |
| 5 | 2 | (N-methyl tetramethylpiperidinyl-N=CH-N- with N-CH₃ tetramethylpiperidine) | $-NH-(CH_2)_6-NH-$ | 176-179 |
| 6 | 2 | (same as Ex. 3) | piperazine-N,N'-diyl | 297-299 |

-continued
| Example No. | n | A | R₄ | Melting point (°C.) |
|---|---|---|---|---|
| 7 | 2 | 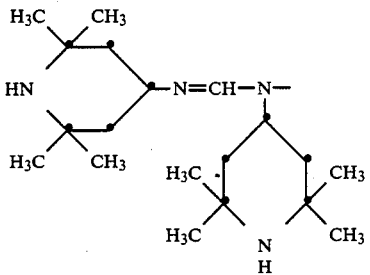 | —NH—(CH₂)₃—NH—(CH₂)₂—NH—(CH₂)₃—NH— | 147–148 |
| 8 | 2 | 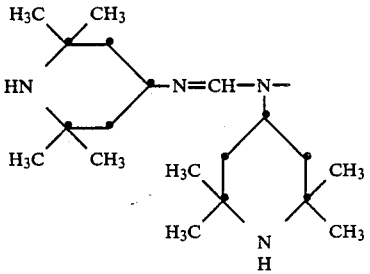 | 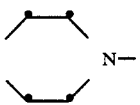 | 208–211 |
| 9 | 3 | 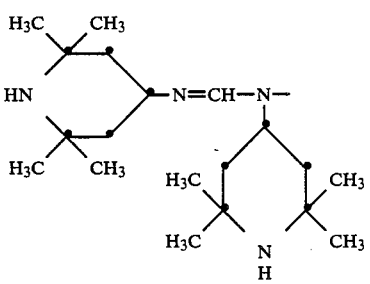 | —NH—(CH₂)₃—N—(CH₂)₂—NH—(CH₂)₃—NH— | 166–170 |
| 10 | 3 | 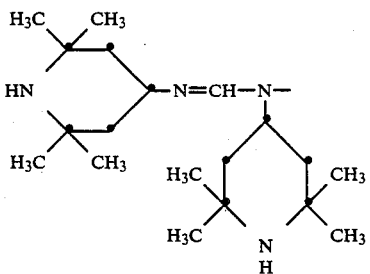 | —NH—(CH₂)₃—N—(CH₂)₃—NH— | 236–240 |
| 11 | 3 | 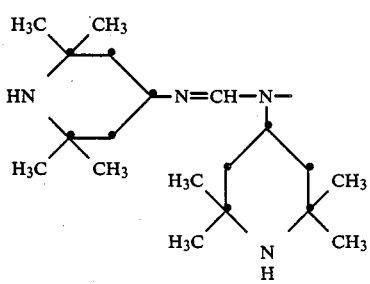 | —NH—(CH₂)₂—N—(CH₂)₂—NH— | 197–200 (crystallized from acetone) |

-continued

| Example No. | n | A | $R_4$ | Melting point (°C.) |
|---|---|---|---|---|
| 12 | 3 | [structure: 2,2,6,6-tetramethylpiperidinyl-HN group linked via N=C(CH$_3$)-N to 2,2,6,6-tetramethyl-4-piperidinyl (NH)] | $-NH-(CH_2)_3-\underset{|}{N}-(CH_2)_3-NH-$ | 129–133 |
| 13 | 3 | [structure: 2,2,6,6-tetramethylpiperidinyl-HN group linked via N=CH-N to 2,2,6,6-tetramethyl-4-piperidinyl (NH)] | $-NH-(CH_2)_3-\underset{|}{N}-(CH_2)_2-NH-$ | 206–209 (crystallized from acetone) |
| 14 | 4 | [structure: 2,2,6,6-tetramethylpiperidinyl-HN group linked via N=CH-N to 2,2,6,6-tetramethyl-4-piperidinyl (NH)] | $-NH-(CH_2)_3-\underset{|}{N}-(CH_2)_2-\underset{|}{N}-(CH_2)_3-NH-$ | 193–196 |

EXAMPLE 15

(A) Preparation of N,N'-bis-(2,4-dichloro-1,3,5-triazin-6-yl)-N,N'-bis-(2,2,6,6-tetramethyl-4-piperidinyl)-1,6-hexanediamine 39.4 g (0.1 mol) of N,N'-bis-(2,2,6,6-tetramethyl-4-piperidinyl)-1,6-hexanediamine dissolved in 150 ml of acetone are added slowly at −10° to −5° C. to 36.9 g (0.2 mol) of cyanuric chloride dissolved in 700 ml of acetone.

After the end of the addition, the mixture is stirred for ½ hour at 0° C., and a solution of 8.4 g (0.21 mol) of sodium hydroxide in 25 ml of water is then added, maintaining the temperature at 0° C.

After the end of the addition, the mixture is stirred for one hour at 0° C. and left to stand overnight.

The precipitate is filtered off and washed with water until free of chloride anions.

After drying, the solid obtained has a melting point of >340° C.

Analysis for $C_{30}H_{48}Cl_4N_{10}$. Calculated: Cl 20.53%. Found: Cl 20.61%.

(B) Preparation of N,N'-bis-[2,4-bis-[N'',N'''-bis-(2,2,6,6-tetramethyl-4-piperidinyl)-formamidino]-1,3,5-triazin-6-yl]-N,N'-bis-(2,2,6,6-tetramethyl-4-piperidinyl)-1,6-hexanediamine 34.53 g (0.05 mol) of N,N'-bis-(2,4-dichloro-1,3,5-triazin-6-yl)-N,N'-bis-(2,2,6,6-tetramethyl-4-piperidinyl)-1,6-hexanediamine, 64.5 g (0.2 mol) of N,N'-bis-(2,2,6,6-tetramethyl-4-piperidinyl-formamidine, 10 g (0.25 mol) of sodium hydroxide and 500 ml of xylene are heated for 4 hours at 70° C. and subsequently heated for 3 hours under reflux and then for further 16 hours while separating off the water of reaction.

The mixture is filtered hot and evaporated in vacuo ~26.7 mbar and the residue is washed with warm acetone.

The product thus obtained has, after drying, a melting point of 283°–286° C.

Analysis for $C_{106}H_{196}N_{26}$. Calculated: C 69.38%; H 10.77%; N 19.85%. Found: C 69.11%; H 10.72%; N 19.89%.

EXAMPLE 16

(A) Preparation of 2-chloro-4-allylamino-6-[N,N'-bis-(2,2,6,6-tetramethyl-4-piperidinyl)-formamidino]-1,3,5-triazine 11.42 g (0.2 mol) of allylamine are added slowly to a solution of 36.88 g (0.2 mol) of cyanuric chloride dissolved in 300 ml of xylene, keeping the temperature between −15° C. and −10° C. After the end of the addition, the mixture is stirred for 1 hour at room temperature.

64.51 g (0.2 mol) of N,N'-bis-(2,2,6,6-tetramethyl-4-piperidinyl)-formamidine are then added slowly and the mixture is heated for 4 hours at 70°–80° C.

20.0 g (0.5 mol) of NaOH are added and the mixture is heated again for 8 hours at 80° C.

The mixture is then filtered off and the solution so obtained is crystallized from n-octane giving a product with melting point of 159°–160° C.

Analysis for $C_{25}H_{43}ClN_8$. Calculated: Cl 7.22%. Found: Cl 7.12%.

(B) Preparation of
N,N'-bis-[2-allylamino-4-[N'',N'''-bis-(2,2,6,6-tetramethyl-4-piperidinyl)-formamidino]-1,3,5-triazin-6-yl]-N,N'-bis-(2,2,6,6-tetramethyl-4-piperidinyl)-1,6-hexanediamine 49.11 g (0.1 mol) of 2-chloro-4-allylamino-6-[N,N'-bis-(2,2,6,6-tetramethyl-4-piperidinyl)-formamidino]-1,3,5-triazine, 19.73 g (0.05 mol) of N,N'-bis-(2,2,6,6-tetramethyl-4-piperidinyl)-1,6-hexanediamine, 6.0 g (0.15 mol) of sodium hydroxide and 500 ml of xylene are heated for 16 hours while separating off the water of reaction. The mixture is filtered off and evaporated in vacuo (23 mbar). The residue is washed with acetone and crystallized by 2-butanone and water. The product obtained has, after drying, a melting point of 230°–232° C.

Analysis for $C_{74}H_{134}N_{20}.2H_2O$. Calculated: C 66.33%; H 10.38%; N 20.91%. Found: C 66.25%; H 10.25%; N 20.80%.

EXAMPLE 17

(A) Preparation of
2-chloro-4-di-n-butylamino-6-[N,N'-bis-(2,2,6,6-tetramethyl-4-piperidinyl)-formamidino]-1,3,5-triazine 15.51 g (0.12 mol) of di-n-butylamine are added slowly to a solution of 22.13 g (0.12 mol) of cyanuric chloride in 150 ml of xylene cooled to −35° C., the temperature being maintained between −35° C. and −30° C. After the end of the addition, the mixture is stirred for 1 hour at the a.m. temperature and, finally, heated to −10° C.

A solution of 4.8 g (0.12 mol) of sodium hydroxide in 25 ml of water is added at −10° C.

After the end of the addition, the mixture is stirred for 1 hour at 20° C., the aqueous solution is separated off and 38.7 g (0.12 mol) of N,N'-bis-(2,2,6,6-tetramethyl-4-piperidinyl)-formamidine are added slowly to the xylene solution maintaining the temperature at 20°–25° C.

After the end of the addition, the mixture is heated for 2 hours at 70° C., cooled to room temperature and added slowly to 5.2 g (0.13 mol) of sodium hydroxide in 16 ml of water.

After the addition, the organic solution is separated off, washed with water, dried over sodium sulfate and filtered.

After evaporation of the solvent, the solid is crystallized from ethyl acetate. The product has a melting point of 131°–133° C.

Analysis for $C_{30}H_{55}ClN_8$. Calculated: Cl 6.29%. Found: Cl 6.26%.

(B) Preparation of
N,N'-bis-[2-di-n-butylamino-4-[N'',N'''-bis-(2,2,6,6-tetramethyl-4-piperidinyl)-formamidino]-1,3,5-triazin-6-yl]-1,6-hexanediamine 56.33 g (0.1 mol) 2-chloro-4-di-n-butylamino-6-[N,N'-bis-(2,2,6,6-tetramethyl-4-piperidinyl)-formamidino]-1,3,5-triazine, 4.4 g (0.11 mol) of ground NaOH and 250 ml of xylene are heated for 3 hours under reflux and further 16 hours while separating off the water of reaction.

The mixture is then evaporated under vacuum (26.6 mbar) and the solid obtained is washed with water and dried at 120° C. under vacuum (2 mbar).

The product has a melting point of 68°–70° C.

Analysis for $C_{66}H_{12}N_{18}$. Calculated: C 67.76%; H 10.68%, N 21.55%. Found: C 67.25%; H 10.67%; N 21.55%.

EXAMPLES 18–19

Following the procedure described in example 17, the following compounds of the formula

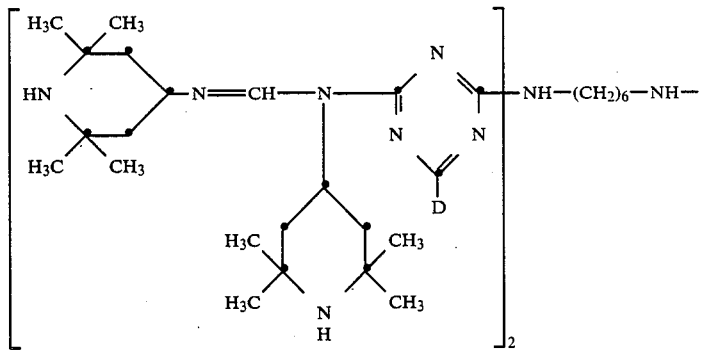

are prepared.

| Example No. | D | Melting point (°C.) |
|---|---|---|
| 18 | —N⌬O (morpholino) | 121–123 |
| 19 | —NH—$(CH_2)_3$—O—$C_2H_5$ | 80–82 |

EXAMPLE 20

2.5 g of each of the compounds indicated in Table 1, 0.25 g of tris-(2,4-di-t-butylphenyl)phosphite, 0.5 g of calcium monoethyl 3,5-di-t-butyl-4-hydroxybenzylphosphonate, 1 g of calcium stearate and 2.5 g of titanium dioxide are mixed in a powder mixer with 1000 g of polypropylene powder (melt index=12 g/10 min; measured at 230° C. and 2.16 kp).

The mixtures are extruded at 200°–220° C. to give polymer granules which are then converted into fibres, using a semitechnical-scale apparatus (Leonard, Sumirage (VA)-Italy), under the following working conditions:
  Extruder temperature: 200°–230° C.
  Head temperature: 255°–260° C.
  Stretch ratio: 1:3.5
  Titre: 11 dtex per filament The fibres thus prepared are exposed, mounted on a white card, in a 65 WR model Weather-O-meter (ASTM G 26-77) at a black panel temperature of 63° C.

The residual tenacity is measured on samples, taken after various times of exposure to the light, by means of a constant-speed tensometer; the exposure time in hours needed to halve the initial tenacity ($T_{50}$) is then calculated.

For comparison, fibres prepared under the same conditions as indicated above, but without the addition of the compounds of the invention, are exposed.

The results are shown in Table 1.

TABLE 1

| Stabilizer | $T_{50}$ (hours) |
| --- | --- |
| Without stabilizer | 150 |
| Compound of example 1 | 2000 |
| Compound of example 2 | 1900 |
| Compound of example 3 | 2100 |
| Compound of example 4 | 1700 |
| Compound of example 10 | 1700 |
| Compound of example 11 | 2030 |
| Compound of example 13 | 1780 |
| Compound of example 14 | 1700 |

EXAMPLE 21

1.0 g of each of the compounds indicated in Table 2, 0.3 g of octadecyl 3-(3',5'-di-t-butyl-4'-hydroxyphenyl)-propionate and 0.1 g of calcium stearate are intimately mixed with 1000 g of low-density polyethylene powder (melt index=0.6 g/10 min; measured at 190° C. and 2.16 kp).

The mixture obtained is then extruded at a temperature of 190° C. and converted into granules, from which thin sheets of 0.2 mm thickness are obtained by melting under pressure at 170° C., and these are exposed on a white card in a 65 WR model Weather-O-meter (ASTM G 26-77) at a black panel temperature of 63° C.

The time in hours ($T_{0.1}$) needed for the carbonyl group content to increase to 0.1%, measured at 5.85 micrometers, is determined on the exposed samples.

For comparison, a thin sheet of polymer is prepared and exposed to light under the same conditions as indicated above, but without the addition of stabilizers prepared according to the invention.

The results obtained are shown in Table 2.

TABLE 2

| Stabilizer | $T_{0.1}$ (hours) |
| --- | --- |
| Without stabilizer | 440 |
| Compound of example 2 | 3800 |
| Compound of example 12 | 3680 |
| Compound of example 13 | 3840 |
| Compound of example 14 | 3750 |
| Compound of example 15 | 3850 |

We claim:
1. A compound of formula (I)

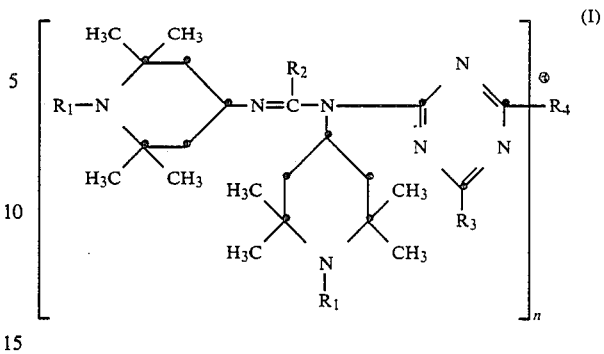

in which $R_1$ is hydrogen, O·, CN, NO, cyanomethyl, $C_1$–$C_{12}$-alkyl, $C_3$–$C_{12}$-alkenyl or $C_3$–$C_{12}$-alkynyl, with the proviso that the carbon atom attached to the nitrogen atom is a primary carbon atom, $C_7$–$C_{12}$-aralkyl, $C_1$–$C_{12}$-acyl, 2,3-epoxypropyl, 2,3-dihyroxypropyl or OH-monosubstituted $C_2$–$C_6$-alkyl, $R_2$ is hydrogen, $C_1$–$C_{18}$-alkyl, $C_5$–$C_{18}$-cycloalkyl, $C_6$–$C_{18}$-aryl or $C_7$–$C_{18}$-aralkyl, $R_3$ is a group

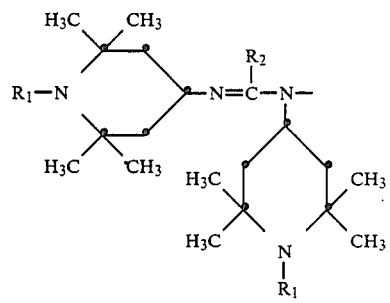

in which $R_1$ and $R_2$ are as defined above, or $R_3$ is a group $R_5X$— in which $R_5$ is hydrogen, $C_1$–$C_{18}$-alkyl, $C_2$–$C_6$-alkyl which is monosubstituted by OH, by $C_1$–$C_{18}$-alkoxy or by $C_2$–$C_{18}$-dialkylamino, $C_5$–$C_{18}$-cycloalkyl, $C_3$–$C_{18}$-alkenyl, $C_6$–$C_{18}$-aryl, $C_7$–$C_{18}$-aralkyl or a group of the formula (II)

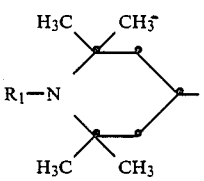

in which $R_1$ is as defined above, and X is —O—, —S— or

with $R_6$ being as defined for $R_5$, or $R_3$ is a 5-membered to 7-membered nitrogen containing heterocyclic group with the free valency on the nitrogen selected from the group consisting of 1-pyrrolidinyl, piperidino, morpholino, 1-hexahydroazepinyl and 4-methyl-1-piperazinyl, and n is an integer from 2 to 6, if n is 2, $R_4$ is a group

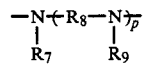

in which p is zero or 1, $R_7$ and $R_9$, which are identical or different, are as defined for $R_5$, and $R_8$ is a direct bond, $C_2$–$C_{18}$-alkylene, $C_5$–$C_{18}$-cycloalkylene, $C_6$–$C_{18}$-arylene, $C_7$–$C_{18}$-aralkylene or $C_4$–$C_{14}$-alkylene which is interrupted in the chain by one or two oxygen atoms or by one or two

groups, in which $R_{10}$ is hydrogen, $C_1$–$C_{12}$-alkyl, $C_6$–$C_{12}$-cycloalkyl or a group of the formula (II), or $R_4$ is the divalent radical of a 5-membered to 7-membered heterocyclic compound with two nitrogen atoms and the free valencies on the nitrogen atoms selected from the group consisting of

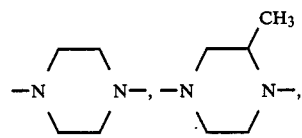

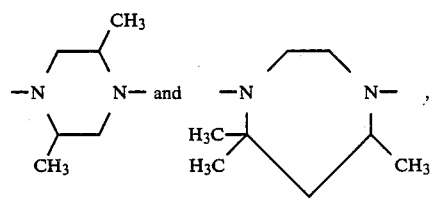

or $R_4$ is

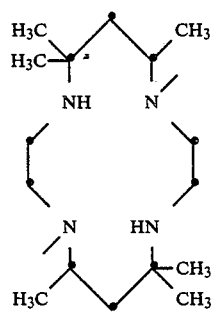

or

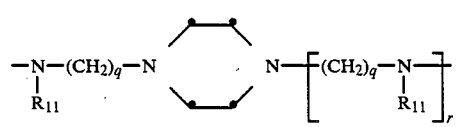

in which $R_{11}$ is as defined for $R_{10}$, q is an integer from 2 to 6 and r is zero or 1, if n is 3, $R_4$ is

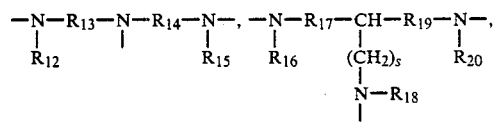

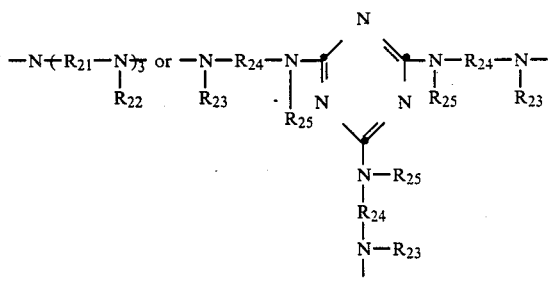

in which $R_{12}$, $R_{15}$, $R_{16}$, $R_{18}$, $R_{20}$, $R_{22}$, $R_{23}$ and $R_{25}$, which are identical or different, are as defined for $R_{10}$, and $R_{13}$ and $R_{14}$, which are identical or different, are $C_2$–$C_{12}$-alkylene or $C_4$–$C_{14}$-alkylene which is interrupted in the chain by an

group, $R_{17}$, $R_{19}$, $R_{21}$ and $R_{24}$, which are identical or different, are $C_2$–$C_{12}$-alkylene and s is zero or 1, if n is 4, 5 or 6, $R_4$ is a group

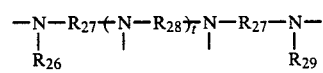

in which $R_{26}$ and $R_{29}$, which are identical or different, are as defined for $R_{10}$, and $R_{27}$ and $R_{28}$, which are identical or different, are $C_2$–$C_{12}$-alkylene and t is 1, 2 or 3, or, if n is 4, $R_4$ is additionally a group

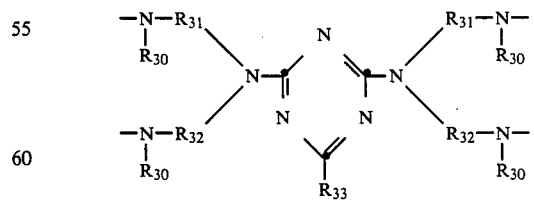

in which $R_{30}$ is as defined for $R_{10}$, $R_{31}$ and $R_{32}$, which are identical or different, are $C_2$–$C_{12}$-alkylene and $R_{33}$ is as defined for $R_3$, or, if n is 6, $R_4$ is additionally a group

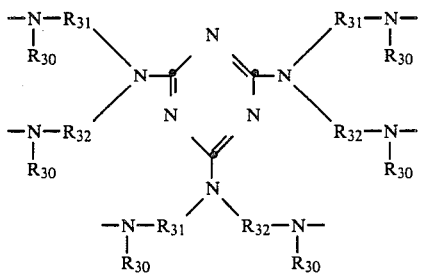

in which R$_{30}$, R$_{31}$ and R$_{32}$ are as defined above.

2. The compound according to claim 1, wherein R$_1$ is hydrogen, methyl, allyl, benzyl or acetyl, R$_2$ is hydrogen, C$_1$-C$_{12}$-alkyl, C$_6$-C$_9$-cycloalkyl or C$_6$-C$_9$-alkyl, R$_3$ is a group

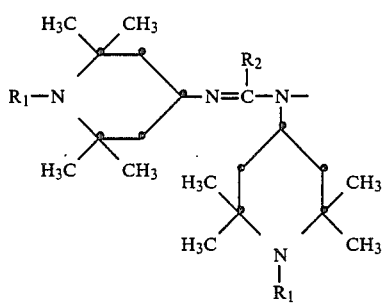

in which R$_1$ and R$_2$ are as defined above, a group R$_5$X— with R$_5$ being hydrogen, C$_1$-C$_8$-alkyl, C$_6$-C$_9$-cycloalkyl, allyl or a group of the formula (II) and X being —O— or

where R$_6$ is hydrogen, C$_1$-C$_8$-alkyl, C$_6$-C$_9$-cycloalkyl, allyl or a group of the formula (II), or R$_3$ is 1-pyrrolidinyl, piperidino, morpholino or 1-hexahydroazepinyl and n is an integer from 2 to 6, and, if n is 2, R$_4$ is a group

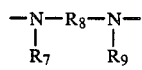

in which R$_7$ and R$_9$, which are identical or different, are hydrogen, C$_1$-C$_{12}$-alkyl, C$_6$-C$_9$-cycloalkyl, allyl or a group of the formula (II) and R$_8$ is C$_2$-C$_6$-alkylene, C$_6$-C$_{15}$-cycloalkylene, phenylene, xylylene or C$_4$-C$_{12}$-alkylene which is interrupted in the chain by one or two oxygen atoms or by one or two

groups, or R$_4$ is

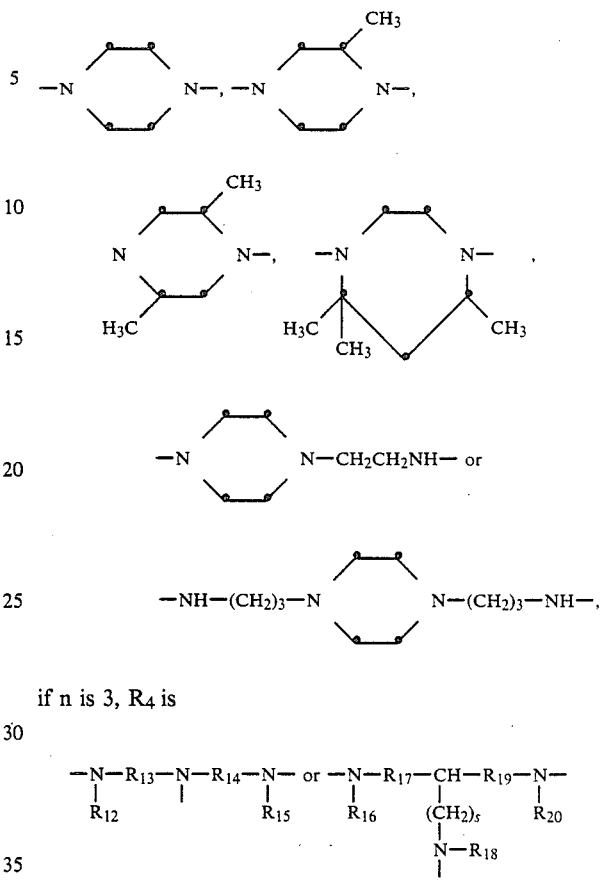

if n is 3, R$_4$ is

in which R$_{12}$, R$_{15}$, R$_{16}$, R$_{18}$ and R$_{20}$, which are identical or different, are hydrogen, C$_1$-C$_{12}$-alkyl, C$_6$-C$_9$-cycloalkyl or a group of the formula (II), R$_{13}$ and R$_{14}$, which are identical or different, are C$_2$-C$_6$-alkylene or C$_4$-C$_6$-alkylene which is interrupted in the chain by an

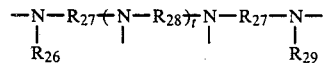

group, R$_{17}$ and R$_{19}$, which are identical or different, are C$_2$-C$_6$-alkylene and s is zero or 1, if n is 4, 5 or 6, R$_4$ is a group —N—R$_{27}$—(N—R$_{28}$)$_t$—N—R$_{27}$—N—
 |                              |
 R$_{26}$                       R$_{29}$ in which R$_{26}$ and R$_{29}$, which are identical or different, are hydrogen, C$_1$-C$_{12}$-alkyl, C$_6$-C$_9$-cycloalkyl or a group of the formula (II), R$_{27}$ and R$_{28}$, which are identical or different, are C$_2$-C$_6$-alkylene and t is 1, 2 or 3.

3. The compound according to claim 1, wherein R$_1$ is hydrogen or methyl, R$_2$ is hydrogen or methyl, R$_3$ is a group

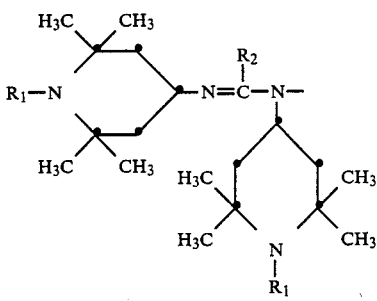

in which $R_1$ and $R_2$ are hydrogen or methyl and n is an integer from 2 to 4, and, if n is 2, $R_4$ is a group

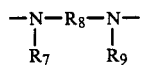

in which $R_7$ and $R_9$, which are identical or different, are hydrogen, $C_1$–$C_4$-alkyl, cyclohexyl, 2,2,6,6-tetramethyl-4-piperidinyl or 1,2,2,6,6-pentamethyl-4-piperidinyl and $R_8$ is $C_2$–$C_6$-alkylene, $C_6$–$C_{13}$-cycloalkylene or $C_4$–$C_{12}$-alkylene which is interrupted in the chain by one or two oxygen atoms or by one or two

groups, or $R_4$ is

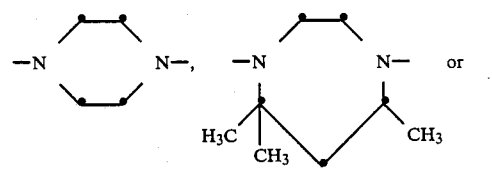

if n is 3, $R_4$ is a group

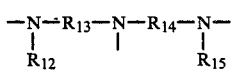

in which $R_{12}$ and $R_{15}$, which are identical or different, are hydrogen, $C_1$–$C_4$-alkyl, cyclohexyl, 2,2,6,6-tetramethyl-4-piperidinyl or 1,2,2,6,6-pentamethyl-4-piperidinyl, and $R_{13}$ and $R_{14}$, which are identical or different, are $C_2$–$C_6$-alkylene or $C_4$–$C_6$-alkylene which is interrupted in the chain by an

group, if n is 4, $R_4$ is a group

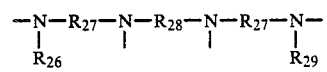

in which $R_{26}$ and $R_{29}$, which are identical or different, are hydrogen, $C_1$–$C_4$-alkyl, cyclohexyl, 2,2,6,6-tetramethyl-4-piperidinyl or 1,2,2,6,6-pentamethyl-4-piperidinyl, and $R_{27}$ and $R_{28}$, which are identical or different, are $C_2$–$C_6$-alkylene.

4. The compound according to claim 1, wherein $R_1$ and $R_2$ are hydrogen, $R_3$ is a group

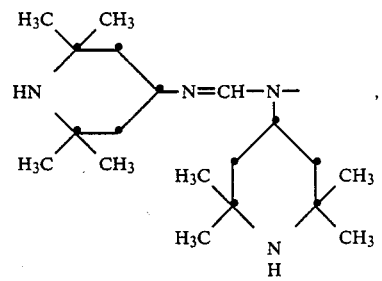

n is 2, 3 or 4, and
if n is 2, $R_4$ is a group

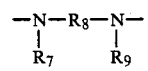

in which $R_7$ and $R_9$, which are identical or different, are hydrogen, methyl or 2,2,6,6-tetramethyl-4-piperidinyl and $R_8$ is —$(CH_2)_{2-6}$—, methylenedicyclohexylene, 4,7-dioxadecane-1,10-diyl or 4,7-diazadecane-1,10-diyl, or $R_4$ is a group

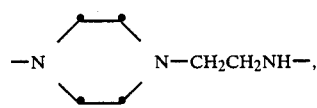

if n is 3, $R_4$ is a group

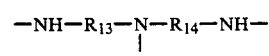

in which $R_{13}$ is a group —$(CH_2)_{2-3}$— and $R_{14}$ is a group —$(CH_2)_{2-3}$— or 3-azahexane-1,6-diyl, and, if n is 4, $R_4$ is a group

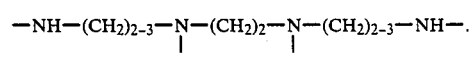

5. The compound according to claim 1, wherein $R_1$ and $R_2$, which are identical or different, are hydrogen or methyl, $R_3$ is a group

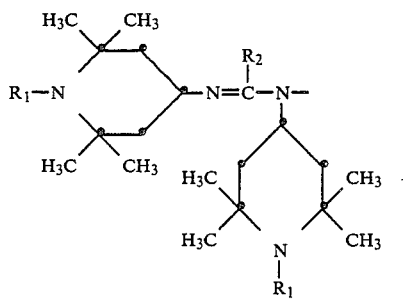

in which $R_1$ and $R_2$ are as defined above or $R_3$ is a group $R_5X$— in which $R_5$ is $C_1$–$C_8$-alkyl, $C_2$–$C_6$-alkyl which is monosubstituted by $C_1$–$C_6$-alkoxy or is allyl and X is

with $R_6$ being hydrogen or $C_1$–$C_8$-alkyl or $R_3$ is morpholino, and n is an integer from 2 to 4, and, if n is 2, $R_4$ is a group

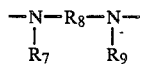

in which $R_7$ and $R_9$, which are identical or different, are hydrogen, $C_1$–$C_4$-alkyl or 2,2,6,6-tetramethyl-4-piperidinyl, $R_8$ is methylenedicyclohexylene, $C_2$–$C_6$-alkylene or $C_4$–$C_{12}$-alkylene which is interrupted in the chain by one or two oxygen atoms or by one or two

or $R_4$ is a group

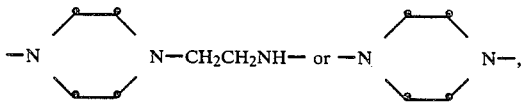

if n is 3, $R_4$ is

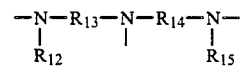

in which $R_{12}$ and $R_{15}$ are hydrogen and $R_{13}$ and $R_{14}$, which are identical or different, are $C_2$–$C_6$-alkylene or $C_4$–$C_6$-alkylene which is interrupted in the chain by one

group, and, if n is 4, $R_4$ is

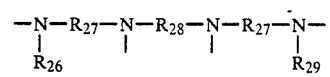

in which $R_{26}$ and $R_{29}$ are hydrogen and $R_{27}$ and $R_{28}$, which are identical or different, are $C_2$–$C_6$-alkylene.

6. The compound N,N'-bis-[2,4-bis-[N'',N'''-bis-(2,2,6,6-tetramethyl-4-piperidinyl)-formamidino]-1,3,5-triazin-6-yl]-1,6-hexanediamine, N,N'-bis-[2,4-bis-[N'',N'''-bis-(2,2,6,6-tetramethyl-4-piperidinyl)-formamidino]-1,3,5-triazin-6-yl]-4,4'-methylene-bis-(cyclohexylamine), N,N'-bis-[2,4-bis-[N'',N'''-bis-(2,2,6,6-tetramethyl-4-piperidinyl)-formamidino]-1,3,5-triazin-6-yl]-N-methyl-1,3-propanediamine, N,N'-bis-[2,4-bis-[N'',N'''-bis-(2,2,6,6-tetramethyl-4-piperidinyl)-formamidino]-1,3,5-triazin-6-yl]-4,7-dioxadecane-1,10-diamine, N,N',N''-tris-[2,4-bis-[N''',N$^{IV}$-bis-(2,2,6,6-tetramethyl-4-piperidinyl)-formamidino]-1,3,5-triazin-6-yl]-3-azapentane-1,5-diamine or N,N',N'',N'''-tetrakis-[2,4-bis-[N$^{IV}$,N$^{V}$-bis-(2,2,6,6-tetramethyl-4-piperidinyl)-formamidino]-1,3,5-triazin-6-yl]-4,7-diazadecane-1,10-diamine according to claim 1.

7. The compound according to claim 1, wherein n is 2, 3 or 4.

8. The compound according to claim 1, wherein $R_1$ and $R_2$ are independently hydrogen or methyl.

9. The compound according to claim 1, wherein $R_3$ is a group

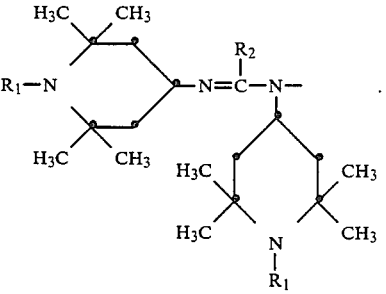

* * * * *